US012810987B2

(12) United States Patent
Tailor

(10) Patent No.: US 12,810,987 B2
(45) Date of Patent: Nov. 24, 2026

(54) BIOMETRIC ACTIVITY APPLICATION FOR GENERATING A BIOMETRIC ACTIVITY PLAN

(71) Applicant: Google LLC, Mountain View, CA (US)

(72) Inventor: Shyam Anil Tailor, London (GB)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 18/425,826

(22) Filed: Jan. 29, 2024

(65) Prior Publication Data

US 2025/0246287 A1 Jul. 31, 2025

(51) Int. Cl.
*G16H 20/30* (2018.01)
*G16H 50/20* (2018.01)

(52) U.S. Cl.
CPC ............. *G16H 20/30* (2018.01); *G16H 50/20* (2018.01)

(58) Field of Classification Search
CPC ............................... G16H 20/30; G16H 50/20
See application file for complete search history.

(56) References Cited

U.S. PATENT DOCUMENTS

2011/0281249 A1 11/2011 Gammell et al.
2015/0317573 A1 11/2015 Petitclerc et al.
2018/0240552 A1 8/2018 Tuyl et al.
2021/0052170 A1* 2/2021 Stewart .................. A61B 5/746
2023/0145042 A1 5/2023 Nikolskiy et al.
2023/0259705 A1 8/2023 Tunstall-Pedoe et al.
2024/0207682 A1* 6/2024 Matsimanis ......... A61B 5/1123
2025/0054623 A1 2/2025 Yellowlees et al.
2025/0157623 A1* 5/2025 Kurani ................. A61B 5/7275

FOREIGN PATENT DOCUMENTS

CN 116705238 9/2023

OTHER PUBLICATIONS

International Search Report and Written Opinion for Application No. PCT/US2025/012732, mailed Apr. 11, 2025, 19 pages.
AI Blog, "Structured Outputs", https://docs.llamaindex.ai/en/v0.9.10/optimizing/advanced_retrieval/structured_outputs/structured_outputs.html#structured-outputs, Retrieved on Jan. 29, 2024, 2 pages.
International Preliminary Report on Patentability for Application No. PCT/US2025/012732, mailed Aug. 13, 2026, 12 pages.

* cited by examiner

*Primary Examiner* — Maroun P Kanaan
(74) *Attorney, Agent, or Firm* — DORITY & MANNING, P.A.

(57) ABSTRACT

A computing system includes one or more memories to store one or more instructions and one or more processors. The one or more processors execute the one or more instructions to perform operations, the operations including: obtaining input data associated with generating a biometric activity plan, implementing one or more machine-learned models to generate the biometric activity plan based on the input data, converting the biometric activity plan to a structured data representation, analyzing features from the structured data representation to determine whether predetermined validity criteria are satisfied, and in response to determining the predetermined validity criteria are satisfied, outputting the biometric activity plan.

19 Claims, 8 Drawing Sheets

4100

```
@dataclasses.dataclass
class Exercise:
    """A single exercise with a duration and notes."""
    action: Action
    duration: Optional[int]
    notes: str = ''


@dataclasses.dataclass
class CompoundExercise:
    """A group of exercises that are repeated."""
    exercises: list[Exercise]

    repetitions: int


@dataclasses.dataclass
class StructuredDailyPlan:
    """A daily workout plan with a list of activities to be performed on that day."""
    activities: list[Union[Exercise, CompoundExercise]]
    description: str
```

FIG. 4A

4200

```
def calculate_total_load(weekly_plan: Iterable[StructuredDailyPlan]) -> int:
    """Calculate the training load over the days provided."""
    total_load = 0
    for daily_plan in weekly_plan:
        for activity in daily_plan.activities
            if isinstance(activity, Exercise):
                total_load += activity.duration
            elif isinstance(activity, CompoundExercise):
                for exercise in activity.exercises:
                    total_load += exercise.duration * activity.repetitions
    return total_load


def rolling_load_check(workout_plan: List[StructuredDailyPlan]} -> bool:
    "Rolling check to ensure that every 7-day window does not increase the load by more than 15%."""
    for i in range(0, len(workout_plan) - 14 + 1):
        week1 = workout_plan[i:i+7]
        week2 = workout_plan[i+7:i+14]

        if (calculate_total_load(week2) - calculate_total_load(week1)) >
            0.15 * calculate_weekly_load(week1):
          return False

    return True
```

FIG. 4B

BIOMETRIC ACTIVITY APPLICATION FOR GENERATING A BIOMETRIC ACTIVITY PLAN

FIELD

The disclosure relates generally to computing systems. More particularly, the disclosure relates to computing systems which include a biometric activity application that can be used to generate a plan for a biometric activity.

BACKGROUND

Exercise plans, meal plans, dieting plans, and the like, can be created by users or nutritionists, fitness coaches, medical professionals, etc. Obtaining such plans can be time consuming, costly, and inconvenient to a user. Computer generated plans can be inaccurate, unsafe, and not customized towards characteristics of the user, leading to frustration on the part of the user as well as causing the inefficient use of computing resources.

SUMMARY

Aspects and advantages of embodiments of the disclosure will be set forth in part in the following description, or can be learned from the description, or can be learned through practice of the example embodiments.

In an example embodiment, a computing system (e.g., a mobile phone, a smartphone, a biometric computing device, a wearable computing device including a smartwatch or tracker, a server computing device, a laptop, a personal computer, etc.) is provided. The computing system includes one or more memories configured to store one or more instructions; and one or more processors configured to execute the one or more instructions stored in the one or more memories to perform operations, the operations including: obtaining input data associated with generating a biometric activity plan, implementing one or more machine-learned models to generate the biometric activity plan based on the input data, converting the biometric activity plan to a structured data representation, analyzing features from the structured data representation to determine whether predetermined validity criteria are satisfied, and in response to determining the predetermined validity criteria are satisfied, outputting the biometric activity plan.

In some implementations, the operations further include: in response to determining the predetermined validity criteria are not satisfied, implementing the one or more machine-learned models to generate an updated biometric activity plan based on the input data and based on the features from the structured data representation which do not satisfy the predetermined validity criteria.

In some implementations, the computing system further includes a user input component configured to receive an input from a user requesting the biometric activity plan, wherein the input data is obtained in response to receiving the input.

In some implementations, obtaining the input data relating to the biometric activity plan is performed automatically in response to an occurrence of a predetermined event.

In some implementations, the predetermined event includes a determination by the computing system that a user associated with the computing system has experienced a biological change in state.

In some implementations, the biometric activity plan includes one or more activities, the predetermined validity criteria includes a respective threshold level of activity for each activity in the biometric activity plan, and determining whether the predetermined validity criteria are satisfied includes determining, for each activity in the biometric activity plan, whether a level for the activity exceeds the respective threshold level of activity.

In some implementations, the biometric activity plan includes one or more activities, the predetermined validity criteria includes a respective threshold increase in a level of activity for each activity in the biometric activity plan over a predetermined duration of time, and determining whether the predetermined validity criteria are satisfied includes determining, for each activity in the biometric activity plan, whether an increase in a level for the activity over the predetermined duration of time exceeds the respective threshold increase in the level of activity.

In some implementations, the structured data representation is in a JavaScript Object Notation form.

In some implementations, an output corresponding to the biometric activity plan generated by the one or more machine-learned models is decoupled from the biometric activity plan which is output in response to determining the predetermined validity criteria are satisfied.

In some implementations, the operations include, in response to the biometric activity plan being generated, retrieving the predetermined validity criteria from an external computing device.

In some implementations, the biometric activity plan generated by the one or more machine-learned models is in a text format, and converting the biometric activity plan to the structured data representation comprises parsing the biometric activity plan to determine the features included in the structured data representation.

In an example embodiment, a computer-implemented method is provided. The computer-implemented method includes obtaining, by a computing system, input data associated with generating a biometric activity plan, implementing, by the computing system, one or more machine-learned models to generate the biometric activity plan based on the input data, converting, by the computing system, the biometric activity plan to a structured data representation, analyzing, by the computing system, features from the structured data representation to determine whether predetermined validity criteria are satisfied, and in response to determining the predetermined validity criteria are satisfied, outputting, by the computing system, the biometric activity plan.

In some implementations, the method further includes, in response to determining the predetermined validity criteria are not satisfied, implementing the one or more machine-learned models to generate an updated biometric activity plan based on the input data and based on the features from the structured data representation which do not satisfy the predetermined validity criteria.

In some implementations, the computer-implemented method includes receiving, via a user input component of the computing system, an input from a user requesting the biometric activity plan, wherein the input data is obtained in response to receiving the input.

In some implementations, obtaining the input data relating to the biometric activity plan is performed automatically in response to an occurrence of a predetermined event, and the predetermined event includes a determination by the computing system that a user associated with the computing system has experienced a biological change in state.

In some implementations, the biometric activity plan includes one or more activities, the predetermined validity criteria includes a respective threshold level of activity for each activity in the biometric activity plan, and determining whether the predetermined validity criteria are satisfied includes determining, for each activity in the biometric activity plan, whether a level for the activity exceeds the respective threshold level of activity.

In some implementations, the biometric activity plan includes one or more activities, the predetermined validity criteria includes a respective threshold increase in a level of activity for each activity in the biometric activity plan over a predetermined duration of time, and determining whether the predetermined validity criteria are satisfied includes determining, for each activity in the biometric activity plan, whether an increase in a level for the activity over the predetermined duration of time exceeds the respective threshold increase in the level of activity.

In some implementations, an output corresponding to the biometric activity plan generated by the one or more machine-learned models is decoupled from the biometric activity plan which is output in response to determining the predetermined validity criteria are satisfied.

In some implementations, the computer-implemented method includes, in response to the biometric activity plan being generated, retrieving the predetermined validity criteria from an external computing device.

The computer-implemented method may include further operations to execute other aspects and operations of the computing system as described herein.

In an example embodiment, a non-transitory computer-readable medium which stores instructions that are executable by one or more processors of a computing system is provided. The non-transitory computer-readable medium stores instructions which are executable by one or more processors of the computing system. The instructions include: instructions to cause the one or more processors to perform operations, the operations including: obtaining input data associated with generating a biometric activity plan, implementing one or more machine-learned models to generate the biometric activity plan based on the input data, converting the biometric activity plan to a structured data representation, analyzing features from the structured data representation to determine whether predetermined validity criteria are satisfied, and in response to determining the predetermined validity criteria are satisfied, outputting the biometric activity plan.

The non-transitory computer-readable medium may store additional instructions to execute other aspects and operations of the computing system and computer-implemented method as described herein.

These and other features, aspects, and advantages of various embodiments of the disclosure will become better understood with reference to the following description, drawings, and appended claims. The accompanying drawings, which are incorporated in and constitute a part of this specification, illustrate examples of the disclosure and, together with the description, serve to explain the related principles.

BRIEF DESCRIPTION OF THE DRAWINGS

Detailed discussion of example embodiments directed to one of ordinary skill in the art is set forth in the specification, which makes reference to the appended drawings, in which:

FIG. 4A illustrates an example structured data representation, according to examples of the disclosure.

FIG. 4B illustrates an example analysis pass, according to examples of the disclosure.

DETAILED DESCRIPTION

Figure 1A:
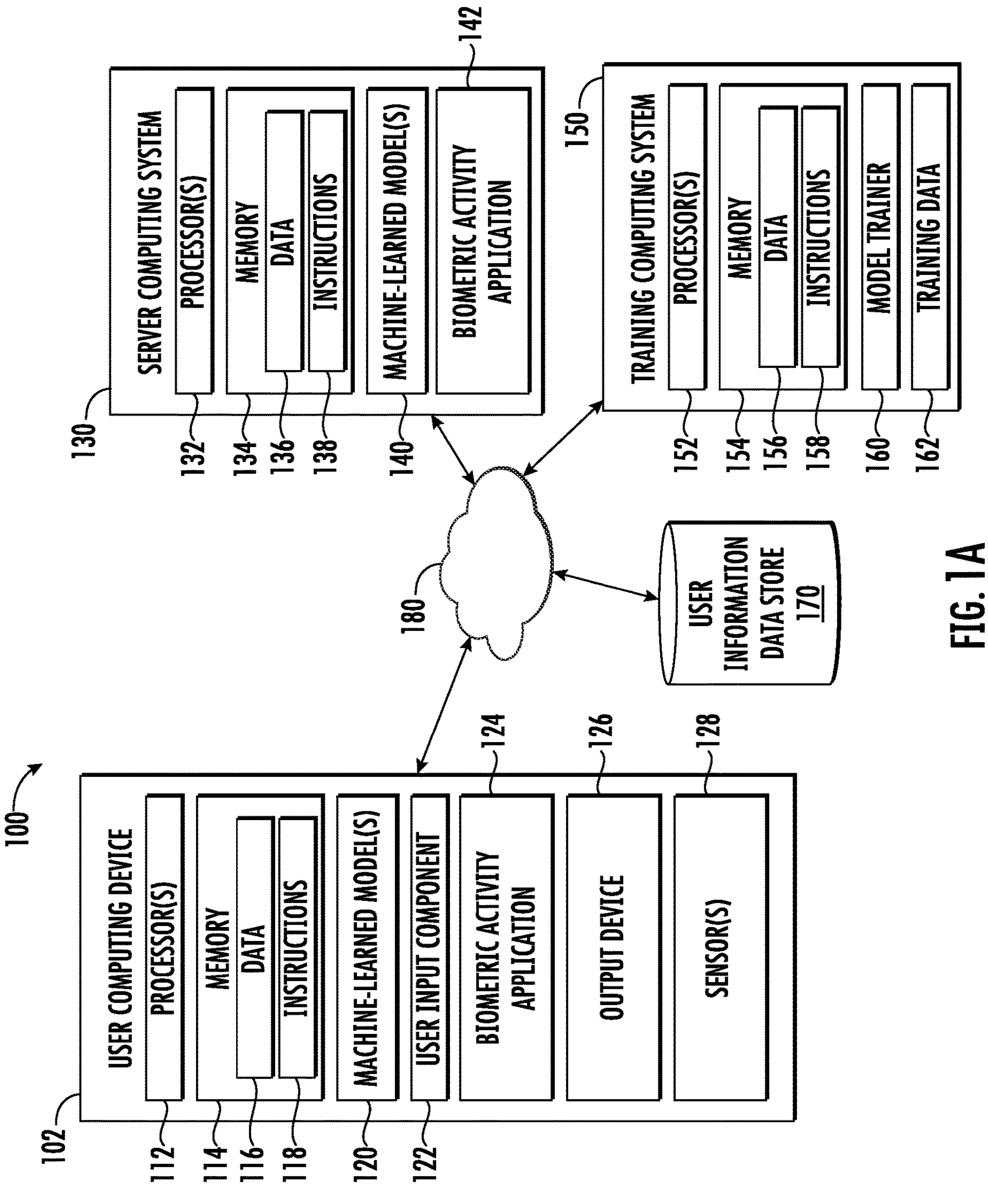
FIG. 1A depicts a block diagram of an example computing system that performs various tasks using a machine-learned model, according to example embodiments of the disclosure.

Reference now will be made to embodiments of the disclosure, one or more examples of which are illustrated in the drawings. Each example is provided by way of explanation of the disclosure and is not intended to limit the disclosure. In fact, it will be apparent to those skilled in the art that various modifications and variations can be made to the disclosure without departing from the scope or spirit of the disclosure. For instance, features illustrated or described as part of one embodiment can be used with another embodiment to yield a still further embodiment. Thus, it is intended that the disclosure covers such modifications and variations as come within the scope of the appended claims and their equivalents.

Terms used herein are used to describe the example embodiments and are not intended to limit and/or restrict the disclosure. The singular forms "a," "an" and "the" are intended to include the plural forms as well, unless the context clearly indicates otherwise. In this disclosure, terms such as "including", "having", "comprising", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, the elements are not limited by these terms. Instead, these terms are used to distinguish one element from another element. For example, without departing from the scope of the disclosure, a first element may be termed as a second element, and a second element may be termed as a first element.

The term "and/or" includes a combination of a plurality of related listed items or any item of the plurality of related listed items. For example, the scope of the expression or phrase "A and/or B" includes the item "A", the item "B", and the combination of items "A and B".

In addition, the scope of the expression or phrase "at least one of A or B" is intended to include all of the following: (1) at least one of A, (2) at least one of B, and (3) at least one of A and at least one of B. Likewise, the scope of the expression or phrase "at least one of A, B, or C" is intended to include all of the following: (1) at least one of A, (2) at least one of B, (3) at least one of C, (4) at least one of A and at least one of B, (5) at least one of A and at least one of C, (6) at least one of B and at least one of C, and (7) at least one of A, at least one of B, and at least one of C.

One method for generating a biometric activity plan (e.g., an exercise plan) may include a computing system implementing one or more machine-learned models (e.g., large language models) to generate the biometric activity plan in an end-to-end fashion (e.g., as raw text).

According to examples of the disclosure, a method for generating a biometric activity plan can include a computing system implementing one or more machine-learned models to generate valid structured data structures and to perform an operation for determining whether certain validity or other criteria are satisfied with respect to the generated biometric activity plan. Therefore, the generated biometric activity plan may be safer and more likely to satisfy expectations of the user.

In some implementations, the structured data structure generated by the computing system may include a structured text output. For example, the structured representation may be in the form of JSON (JavaScript Object Notation) or another type of structured text output.

In some implementations, the computing system may be configured to parse the structured output and determine whether one or more validity criteria are satisfied. The one or more validity criteria may be determined according to a user, according to external sources, etc. An example validity criteria may include ensuring that a training load for a biometric activity does not increase by more than a predetermined amount over a predetermined duration of time (e.g., a training load does not increase by more than 15% over seven days).

When the generated biometric activity plan does not satisfy the one or more validity criteria, the computing system may be configured to reject the biometric activity plan. In some implementations, the process for generating the biometric activity plan may be repeated and a new biometric activity plan may be generated.

Example aspects of the disclosure provide several technical effects, benefits, and/or improvements in computing technology and the technology of computing devices and health monitoring devices. For example, according to one or more examples of the disclosure, biometric activity plans can be generated and provided in an accurate and efficient manner by use of a biometric activity application. The biometric activity application can be configured to determine whether a biometric activity plan initially generated via one or more machine-learned models satisfies validity criteria associated with one or more activities in the biometric activity plan, to ensure that the biometric activity plan is valid, accurate, safe, practical, reasonable, etc. If the biometric activity plan initially generated via the one or more machine-learned models does not satisfy the validity criteria, the biometric activity plan can be rejected. By utilizing the validity criteria to reject biometric activity plans initially generated via the one or more machine-learned models (which the user would have likely rejected had such plans been presented to the user, for example, via a graphical user interface), computing resources can be conserved (e.g., bandwidth, network resources, processing power, etc.) because the computing system will not transmit a biometric activity plan that is not valid and because the user will not have to reject the biometric activity plan and request another biometric activity plan be generated.

For example, according to one or more examples of the disclosure, the biometric activity plan which satisfies the validity criteria can better satisfy user expectations, match user preferences, and be efficiently rendered.

FIG. 1A depicts a block diagram of an example computing system 100 that performs various tasks using one or more machine-learned models (e.g., one or more large language models, one or more generative machine-learned models, etc.) according to example embodiments of the disclosure. The computing system 100 includes a user computing system 102, a server computing system 130, and a training computing system 150 that are communicatively coupled over a network 180.

The user computing system 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing system 102 includes one or more processors 112 and a memory 114. The one or more processors 112 can be any suitable processing device (e.g., a processor core, a microprocessor, an ASIC, an FPGA, a controller, a microcontroller, etc.) and can be one processor or a plurality of processors that are operatively connected. The memory 114 can include one or more non-transitory computer-readable storage media, such as RAM, ROM, EEPROM, EPROM, flash memory devices, magnetic disks, etc., and combinations thereof. The memory 114 can store data 116 and instructions 118 which are executed by the processor 112 to cause the user computing system 102 to perform operations.

In some implementations, the user computing system 102 can store or include one or more machine-learned models 120 (e.g., one or more generative machine-learned models, one or more large language models, etc.). For example, the one or more machine-learned models 120 can be or can otherwise include various machine-learned models such as neural networks (e.g., deep neural networks) or other types of machine-learned models, including non-linear models and/or linear models. Example neural networks can include feed-forward neural networks, recurrent neural networks (RNNs), including long short-term memory (LSTM) based recurrent neural networks, convolutional neural networks (CNNs), diffusion models, generative-adversarial networks, or other forms of neural networks. Example neural networks can be deep neural networks. Some example machine-learned models can leverage an attention mechanism such as self-attention. For example, some example machine-learned models can include multi-headed self-attention models (e.g., transformer models). Example machine-learned models 120 are discussed with reference to the drawings herein.

In some implementations, the one or more machine-learned models 120 can be received from the server computing system 130 over network 180, stored in the memory 114, and then used or otherwise implemented by the one or more processors 112. In some implementations, the user computing system 102 can implement multiple parallel instances of a single machine-learned model 120 (e.g., to perform parallel tasks across multiple instances of the machine-learned model 120). In some implementations, the task is a generative task and one or more machine-learned models may be implemented to output content (e.g., a structured data structure) in view of various inputs (e.g., user data, sensor data, existing biometric activity plans, etc.). More particularly, the machine-learned models disclosed herein (e.g., including large language models, sequence processing models, generative machine-learned models, etc.), may be implemented to perform various tasks related to an input query for a biometric activity plan.

More particularly, the machine-learned models disclosed herein may be implemented to perform various tasks related to generating a biometric activity plan.

According to examples of the disclosure, a computing system may implement one or more sequence processing models as described herein to output values for one or more conditions in response to or based on a query. The one or more sequence processing models may include one or more machine-learned models which are configured to process and analyze sequential data and to handle data that occurs in a specific order or sequence, including time series data, natural language text, or any other data with a temporal or sequential structure.

According to examples of the disclosure, a computing system may implement one or more large language models to determine a plurality of variables based on the query. For example, a large language model may include a Bidirectional Encoder Representations from Transformers (BERT) large language model. The large language model may be trained to understand and process natural language for example. The large language model may be configured to extract information from the input (query) to identify keywords, intents, and context within the input to determine a plurality of variables for generating the biometric activity plan. The variables may include latent variables that represent an underlying structure of the language.

According to examples of the disclosure, a computing system may implement one or more generative machine-learned models to generate the biometric activity plan having values for one or more conditions associated with the biometric activity plan. The one or more generative machine-learned models 3140 may include a deep neural network or a generative adversarial network (GAN) to generate the biometric activity plan having values for one or more conditions associated with the biometric activity plan. For example, the one or more generative machine-learned models 3140 may include variational autoencoders, stable diffusion machine-learned models, etc., to generate the biometric activity plan with values for conditions associated with the biometric activity plan.

Additionally, or alternatively, one or more machine-learned models 140 can be included in or otherwise stored and implemented by the server computing system 130 that communicates with the user computing system 102 according to a client-server relationship. For example, the one or more machine-learned models 140 can be implemented by the server computing system 130 as a portion of a web service (e.g., a recommendation service, a search service, an image analysis service, and the like). Thus, one or more machine-learned models 120 can be stored and implemented at the user computing system 102 and/or one or more machine-learned models 140 can be stored and implemented at the server computing system 130.

The user computing system 102 can also include one or more user input components 122 that receives user input. For example, the user input component 122 can include, for example, one or more of a keyboard (e.g., a physical keyboard, virtual keyboard, etc.), a mouse, a joystick, a button, a switch, an electronic pen or stylus, a gesture recognition sensor (e.g., to recognize gestures of a user including movements of a body part), an input sound device or voice recognition sensor (e.g., a microphone to receive a voice command), a track ball, a remote controller, a portable (e.g., a cellular or smart) phone, a camera, and so on. The user input component 122 may also be embodied by a touch-sensitive display device having a touchscreen capability, for example. The user input component 122 may be used by the user of the user computing system 102 to provide an input to request a biometric activity plan. For example, the input may be a voice input, a touch input, a gesture input, a click via a mouse or remote controller, and so on.

The user computing system 102 can also include an output device 126 configured to provide an output to the user and may include, for example, one or more of an audio device (e.g., one or more speakers), a haptic device to provide haptic feedback to a user, a light source (e.g., one or more light sources such as LEDs which provide visual feedback to a user), a display device, and the like. The display device may include a liquid crystal display (LCD), a light emitting diode (LED) display, an organic light emitting diode (OLED) display, active matrix organic light emitting diode (AMOLED), flexible display, 3D display, a plasma display panel (PDP), a cathode ray tube (CRT) display, and the like, for example. For example, in some implementations of the disclosure the user may be provided with a visual representation of a generated biometric activity plan.

The user computing system 102 can also include a biometric activity application 124. The biometric activity application 124 can include any biometric activity application which allows or is capable of enabling a user to request via a query a biometric activity plan and which allows or is capable of providing the biometric activity plan for the user (e.g., based on the query from the user). In some implementations, the biometric activity application 124 may be configured to measure biometric information associated with a user, for example, while the user performs an activity. The user computing system 102 (biometric activity application 124) may be configured to measure (e.g., via the one or more sensors 128) various biometrics, including biometrics associated with an ECG, PPG, heart rate, heart rate recovery, pulse information, BMI, heart rate variability, blood pressure, oxygen saturation, body temperature, sleep quality, physical activities (e.g., number of steps walked, number of miles cycled, number of laps swam, etc.), and the like. Further, the user computing system 102 (biometric activity application 124) may be configured to generate or display information associated with a measured biometric, including an electrocardiogram, a photoplethysmogram, heart rate, heart rate recovery, blood pressure, oxygen saturation, respiration rate, body temperature, physical activity, a sleep metric, electrical conductance, and the like. Further, the user computing system 102 (biometric activity application 124) may be configured to analyze (e.g., compare) measured biometric information in relation to an activity performed by the user with respect to a generated biometric activity plan (e.g., an exercise workout) to determine whether a user has carried out the biometric activity plan and met certain goals, etc.

For example, in some implementations a user may execute the biometric activity application 124 by providing an input to the user computing system 102 via the user input component 122. Aspects of the biometric activity application 124 are described in further detail herein.

The user computing system 102 can also include one or more sensors 128. For example, the one or more sensors 128 may include an inertial measurement unit which includes one or more accelerometers and/or one or more gyroscopes. The one or more accelerometers may be used to capture motion information with respect to the user computing system 102. The one or more gyroscopes may also be used additionally or alternatively to capture motion information with respect to the user computing system 102. For example, the inertial measurement unit may be configured as a six-axis or six-dimensional inertial measurement unit (e.g., a tri-axial accelerometer and a tri-axial gyroscope). For example, the one or more sensors 128 may include one or more cameras. The one or more cameras may include an imaging sensor (e.g., a complementary metal-oxide-semiconductor (CMOS) or charge-coupled device (CCD)) to capture, detect, or recognize a user's behavior, figure, expression, etc.

For example, the one or more sensors 128 may include one or more optical sensors (e.g., one or more photoplethysmography (PPG) sensors) which can also be used to monitor the heart rate of the user. Additionally, the one or more optical sensors may be configured to provide information about heart rate variability (HRV), blood oxygen saturation (SpO2) levels, and the like. For example, the one or more sensors 128 may include one or more ECG sensors which can also be used to monitor the heart rate of the user. The one or more sensors 128 may also include other sensors such as a magnetometer, GPS sensor, proximity sensor, and the like.

The server computing system 130 includes one or more processors 132 and a memory 134. The one or more processors 132 can be any suitable processing device (e.g., a processor core, a microprocessor, an ASIC, an FPGA, a controller, a microcontroller, etc.) and can be one processor or a plurality of processors that are operatively connected. The memory 134 can include one or more non-transitory computer-readable storage media, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more machine-learned models 140. For example, the machine-learned models 140 can be or can otherwise include various machine-learned models. Example machine-learned models include neural networks or other multi-layer non-linear models. Example neural networks include feed forward neural networks, deep neural networks, recurrent neural networks, and convolutional neural networks. Some example machine-learned models can leverage an attention mechanism such as self-attention. For example, some example machine-learned models can include multi-headed self-attention models (e.g., transformer models). Example machine-learned models 140 are discussed herein with reference to the drawings.

The server computing system 130 can also include a biometric activity application 142. The biometric activity application 142 of the server computing system 130 can include similar features as the biometric activity application 124 which perform similar functions and operations, and therefore a description of those features will not be repeated for the sake of brevity.

The user computing system 102 and/or the server computing system 130 can train the machine-learned models 120 and/or 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, an FPGA, a controller, a microcontroller, etc.) and can be one processor or a plurality of processors that are operatively connected. The memory 154 can include one or more non-transitory computer-readable storage media, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 120 and/or 140 stored at the user computing system 102 and/or the server computing system 130 using various training or learning techniques, such as, for example, backwards propagation of errors. For example, a loss function can be back propagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over a number of training iterations.

In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train the machine-learned models 120 and/or 140 based on a set of training data 162. The training data 162 can include, for example, various datasets which may be stored remotely or at the training computing system 150. For example, in some implementations an example dataset utilized for training includes example biometric activity plans. The training datasets may be categorized according to a type of activity (e.g., a biometric activity plan for running, for swimming, for cycling, for weightlifting, etc.). In other implementations, the training datasets may be confined to particular characteristics of a user (e.g., a particular age, a particular weight, etc.). In some implementations, the dataset may contain diverse subject matter.

In some implementations, if the user has provided consent, the training examples can be provided by the user computing system 102. Thus, in such implementations, the one or more machine-learned models 120 provided to the user computing system 102 can be trained by the training computing system 150 on user-specific data received from the user computing system 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM, hard disk, or optical or magnetic media.

The network 180 can include any type of communications network such as a local area network (LAN), wireless local area network (WLAN), wide area network (WAN), personal area network (PAN), virtual private network (VPN), or the like. For example, wireless communication between elements of the examples described herein may be performed via a wireless LAN, Wi-Fi, Bluetooth, ZigBee, Wi-Fi direct (WFD), ultra wideband (UWB), infrared data association (IrDA), Bluetooth low energy (BLE), near field communication (NFC), a radio frequency (RF) signal, and the like. For example, wired communication between elements of the examples described herein may be performed via a pair cable, a coaxial cable, an optical fiber cable, an Ethernet cable, and the like. Communication over the network can use a wide variety of communication protocols (e.g., TCP/IP, HTTP, SMTP, FTP), encodings or formats (e.g., HTML, XML), and/or protection schemes (e.g., VPN, secure HTTP, SSL).

The machine-learned models described in this specification may be used in a variety of tasks, applications, and/or use cases.

In some implementations, the input to the machine-learned model(s) of the disclosure can be text or natural language data. The machine-learned model(s) can process the text or natural language data to generate an output. As an example, the machine-learned model(s) can process the natural language data to generate a language encoding output. As another example, the machine-learned model(s) can process the text or natural language data to generate a latent text embedding output. As another example, the machine-learned model(s) can process the text or natural language data to generate a translation output. As another example, the machine-learned model(s) can process the text or natural language data to generate a classification output. As another example, the machine-learned model(s) can process the text or natural language data to generate a textual segmentation output. As another example, the machine-learned model(s) can process the text or natural language data to generate a semantic intent output. As another example, the machine-learned model(s) can process the text or natural language data to generate an upscaled text or natural language output (e.g., text or natural language data that is higher quality than the input text or natural language, etc.). As another example, the machine-learned model(s) can process the text or natural language data to generate a prediction output.

In some implementations, the input to the machine-learned model(s) of the disclosure can be speech data. The machine-learned model(s) can process the speech data to generate an output. As an example, the machine-learned model(s) can process the speech data to generate a speech recognition output. As another example, the machine-learned model(s) can process the speech data to generate a speech translation output. As another example, the machine-learned model(s) can process the speech data to generate a latent embedding output. As another example, the machine-learned model(s) can process the speech data to generate an encoded speech output (e.g., an encoded and/or compressed representation of the speech data, etc.). As another example, the machine-learned model(s) can process the speech data to generate an upscaled speech output (e.g., speech data that is higher quality than the input speech data, etc.). As another example, the machine-learned model(s) can process the speech data to generate a textual representation output (e.g., a textual representation of the input speech data, etc.). As another example, the machine-learned model(s) can process the speech data to generate a prediction output.

In some implementations, the input to the machine-learned model(s) of the disclosure can be sensor data. The machine-learned model(s) can process the sensor data to generate an output. As an example, the machine-learned model(s) can process the sensor data to generate a recognition output. As another example, the machine-learned model(s) can process the sensor data to generate a prediction output. As another example, the machine-learned model(s) can process the sensor data to generate a classification output. As another example, the machine-learned model(s) can process the sensor data to generate a segmentation output. As another example, the machine-learned model(s) can process the sensor data to generate a visualization output. As another example, the machine-learned model(s) can process the sensor data to generate a diagnostic output. As another example, the machine-learned model(s) can process the sensor data to generate a detection output.

FIG. 1A illustrates an example computing system that can be used to implement aspects of the disclosure. Other computing systems can be used as well. For example, in some implementations, the user computing system 102 can include the model trainer 160 and the training data 162. In such implementations, the machine-learned models 120 can be both trained and used locally at the user computing system 102. In some of such implementations, the user computing system 102 can implement the model trainer 160 to personalize the machine-learned models 120 based on user-specific data.

Example computing system 100 can also include a user information data store 170. In some implementations, user information data store 170 can represent a single database. In some implementations, the user information data store 170 represents a plurality of different databases accessible to the user computing system 102, server computing system 130, and training computing system 150. In some examples, the user information data store 170 can include biometric information of a user or a plurality of users. In some examples, the user information data store 170 can include information regarding one or more user profiles, including a variety of user data such as user preference data, user demographic data, user calendar data, user social network data, user historical health data, and the like. For example, the user information data store 170 can include any biometric information or information associated with the biometric information (e.g., time information associated with the collection of the biometric information, location information associated with the collection of the biometric information, type of activity information associated with the collection of the biometric information, etc.). The user biometric information and associated information may be associated with a user account.

The user information data store 170 is provided to illustrate potential data that could be analyzed or stored, in some embodiments, by the user computing system 102 and/or server computing system 130 to maintain a record of biometric information associated with a user, for example. However, such user data may not be collected, used, or analyzed unless the user has consented after being informed of what data is collected and how such data is used. Further, in some embodiments, the user can be provided with a tool (e.g., in a biometric activity application or via a user account) to revoke or modify the scope of permissions. In addition, certain information or data can be treated in one or more ways before it is stored or used, so that personally identifiable information is removed or stored in an encrypted fashion. Thus, particular user information stored in the user information data store 170 may or may not be accessible to the user computing system 102 and/or server computing system 130 based on permissions given by the user, or such data may not be stored in the user information data store 170 at all.

Figure 1B:
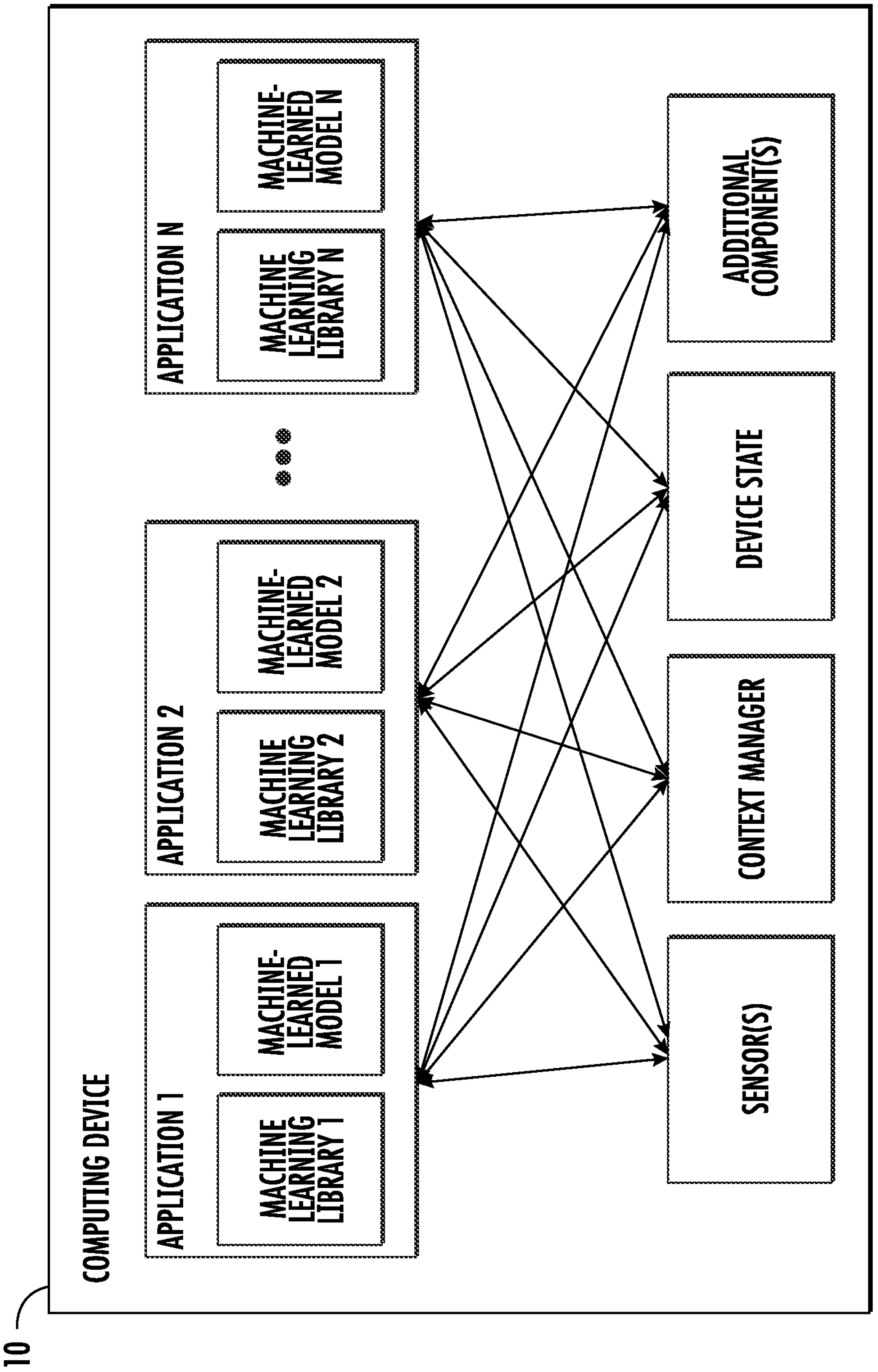
FIG. 1B depicts a block diagram of an example computing device that performs various tasks using a machine-learned model, according to example embodiments of the disclosure.

FIG. 1B depicts a block diagram of an example computing device 10 that performs according to example embodiments of the disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a biometric activity application, a text messaging application, an email application, a dictation application, a virtual keyboard application, a social media application, an infotainment application, a browser application, etc.

As illustrated in FIG. 1B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 1C:
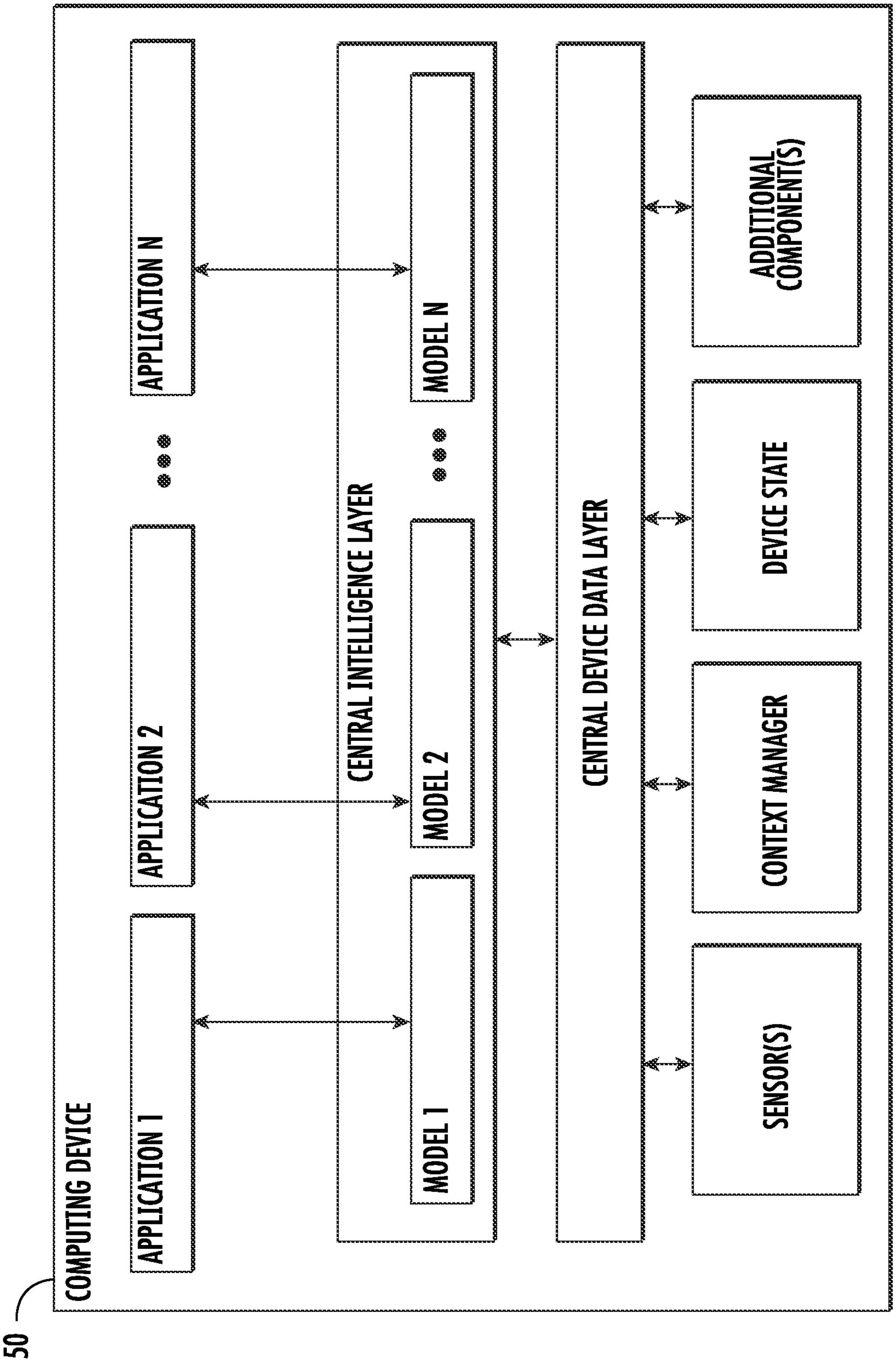
FIG. 1C depicts a block diagram of an example computing device that performs various tasks using a machine-learned model, according to example embodiments of the disclosure.

FIG. 1C depicts a block diagram of an example computing device 50 that performs according to example embodiments of the disclosure. The computing device 50 can be a user computing device or a server computing device.

The computing device 50 includes a number of applications (e.g., applications 1 through N). Each application is in communication with a central intelligence layer. Example applications include a biometric activity application, a text messaging application, an email application, a dictation application, a virtual keyboard application, a social media application, an infotainment application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 1C, a respective machine-learned model can be provided for each application and managed by the central intelligence layer. In other implementations, two or more applications can share a single machine-learned model. For example, in some implementations, the central intelligence layer can provide a single model for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 1C, the central device data layer can communicate with a number of other components of the computing device, such as, for example, one or more sensors, a context manager, a device state component, and/or additional components. In some implementations, the central device data layer can communicate with each device component using an API (e.g., a private API).

Figure 2:
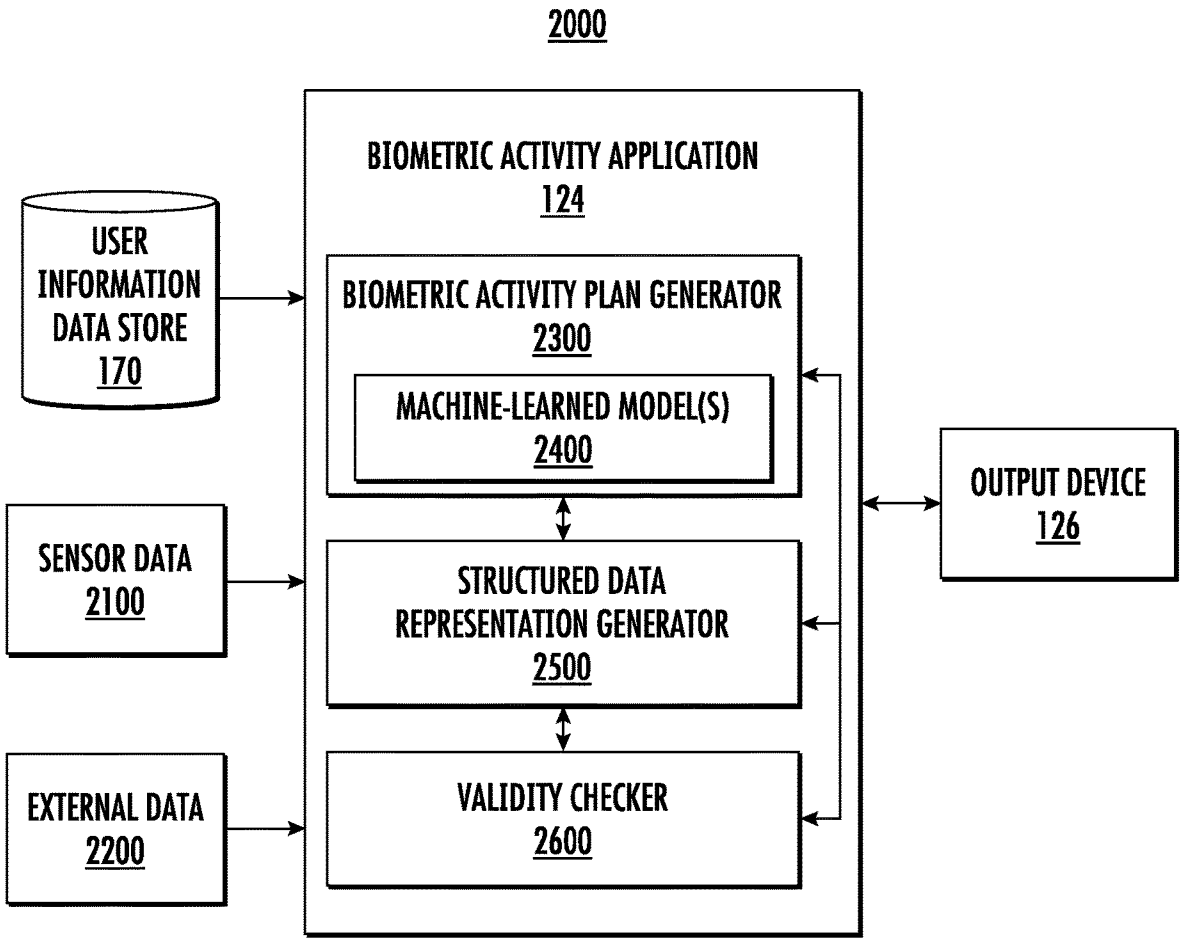
FIG. 2 is an example block diagram of a biometric activity application, according to one or more examples of the disclosure.

Referring to FIG. 2, an example block diagram of a biometric activity application is shown, according to one or more examples of the disclosure. FIG. 2 illustrates that the biometric activity application 124 includes a biometric activity plan generator 2300, a structured data representation generator 2500, and a validity checker 2600. However, the biometric activity application 124 may include fewer or more features than that shown in FIG. 2. For example, any of the features or operations of the components of biometric activity application 124 may be provided separately from the biometric activity application 124. For example, some operations (such as the generation of the structured representation structure by the structured data representation generator 2500) may instead be performed by the server computing system 130 (e.g., via biometric activity application 142).

Figure 3:
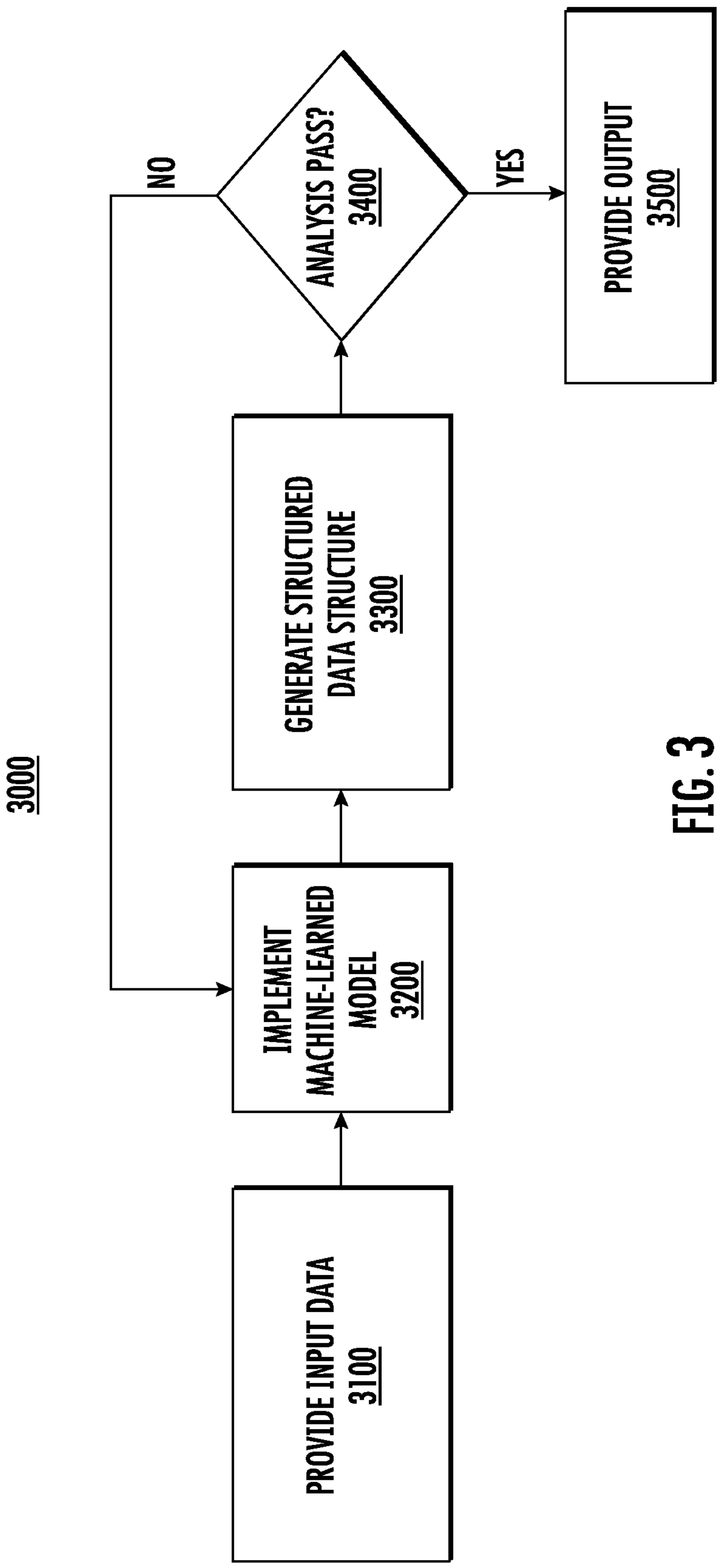
FIG. 3 illustrates an example flow diagram of a non-limiting computer-implemented method for generating a biometric activity plan for a user, according to one or more examples of the disclosure.

Operations of the biometric activity application 124 will now be described in more detail with reference to FIG. 3 and FIGS. 4A-4B. FIG. 3 illustrates an example flow diagram of a non-limiting computer-implemented method for generating a biometric activity plan for a user, according to one or more examples of the disclosure. FIG. 4A illustrates an example structured data representation, according to examples of the disclosure. FIG. 4B illustrates an example analysis pass, according to examples of the disclosure.

The flow diagram of FIG. 3 illustrates a method 3000 for generating a biometric activity plan for a user. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

In some implementations a user may execute the biometric activity application 124 and provide a query requesting a particular biometric activity plan. For example, the user may request an exercise workout plan for lifting weights, an exercise workout plan for swimming, an exercise workout plan for cycling, etc. As another example, the user may request a dieting plan to lose a certain amount of weight, a dieting plan that satisfies certain dietary and/or health restrictions of the user, a dieting plan that specifies the best time to consume food and/or beverages, etc. As another example, the user may request an activity plan related to a sleep schedule for the user, for example, a sleep plan that is in accordance with the user's circadian rhythm.

In some implementations the biometric activity application 124 may be executed automatically by the user computing system 102. For example, the biometric activity application 124 may be executed automatically at a predetermined time (e.g., at a particular time in the morning, in the evening, etc.). For example, the biometric activity application 124 may be executed automatically in response to the occurrence of a particular event. The particular event may include for example, when the user computing system 102 is powered on, in response to determining a user associated with the computing system has experienced a biological change in state such as the user has woken up (hypnopompia), a blood pressure or heartbeat of the user has changed by more than a threshold amount, etc.

At operation 3100 the method 3000 includes providing input data to the computing system. For example, the computing system can include the user computing system 102 and/or server computing system 130. For example, the input data can be provided to biometric activity application 124. The input data may include information from a query provided by a user, information from the user information data store 170, information associated with the sensor data 2100, and/or information associated with the external data 2200.

For example, the user information data store 170 can include information regarding one or more user profiles, including a variety of user data such as user preference data, user demographic data, user calendar data, user social network data, user historical health data, and the like. For example, the user information data store 170 can include any biometric information or information associated with the biometric information (e.g., time information associated with the collection of the biometric information, location information associated with the collection of the biometric information, type of activity information associated with the collection of the biometric information, etc.). The user biometric information and associated information may be associated with a user account.

For example, the sensor data 2100 can include information collected via the one or more sensors 128. For example, the sensor data 2100 can include data related to various biometrics, including biometrics associated with an ECG, PPG, heart rate, heart rate recovery, pulse information, BMI, heart rate variability, blood pressure, oxygen saturation, body temperature, sleep quality, physical activities (e.g., number of steps walked, number of miles cycled, number of laps swam, etc.), and the like.

For example, the external data 2200 can include information collected from one or more external sources (e.g., another computing device, another server computing system, another database, websites, etc.). The one or more external sources can provide information for generating biometric activity plans, including existing biometric activity plans, information relating to validity criteria that may be used for generating a particular biometric activity plan for a particular activity, etc.

At operation 3200, one or more machine-learned models may be implemented to generate an initial biometric activity plan based on the input data. For example, the one or more machine-learned models 2400 of the biometric activity plan generator 2300 may be configured to generate, based on the input data, an output which includes a biometric activity plan. The one or more machine-learned models 2400 may correspond to the one or more machine-learned models 120, for example.

In some implementations, the one or more machine-learned models 2400 may be configured to generate a biometric activity plan in a particular format. For example, the particular format may be a format that can be converted into a structured data representation. For example, the biometric activity plan may be in a text form and can be converted to the structured data representation. The output provided by the one or more machine-learned models 2400 may be different from the output that is provided to the user at operation 3500 (e.g., via a display device, via speaker, etc.). That is the output provided by the one or more machine-learned models 2400 and the output that is rendered to the user (e.g., via output device 126) are decoupled.

At operation 3300, the method 3000 may include generating a structured data structure based on the biometric activity plan that is generated. For example, the structured data representation generator 2500 may be configured to convert text (e.g., corresponding to the biometric activity plan) output by the one or more machine-learned models 2400 by parsing the text using string manipulation or regular expressions to extract relevant information from the text. For example, certain information may be extracted and mapped to a particular dictionary to hold the extracted information. As an example, if a biometric activity plan output in text form by the one or more machine-learned models 2400 is descriptive of performing an exercise for two minutes, the dictionary used to generate the structured data representation may have an object that corresponds to a "duration" with a property that has a value of "two minutes". In some implementations, the structured data structure (representation) may be in a JSON (JavaScript Object Notation) structured data format.

In some implementations, the structured data representation generated by the structured data representation generator 2500 may be loaded into a programming language (e.g., Python) using built-in libraries to obtain another data structure corresponding to the programming language (e.g., a Python data structure).

FIG. 4A illustrates an example structured data representation, according to examples of the disclosure. The example structured data representation 4100 includes data classes configured to represent different aspects of a workout plan, from individual exercises to compound exercises and the overall daily plan. The use of data classes simplifies the creation and management of these classes by automatically generating special methods based on the defined attributes.

For example, the structured data representation 4100 includes an "Exercise" class defined using the dataclasses module and is configured to hold structured data representing a single exercise having two attributes (e.g., "action" and "duration" representing the duration of the exercise). For example, the structured data representation 4100 includes a "CompoundExercise" class defined using the dataclasses module and is configured to hold structured data representing a group of exercises having two attributes (e.g., "exercises" and "repetitions" representing the number of repetitions of the exercise).

For example, the structured data representation 4100 defines a data structure and functions related to a structured daily workout plan using Python code. The example structured data representation includes a class ("StructuredDailyPlan") that is defined using the dataclasses module and is configured to hold structured data having two attributes (e.g., "activities" and "description").

At operation 3400 the method 3000 may include performing an analysis with respect to the structured data representation generated by the structured data representation generator 2500. For example, the validity checker 2600 may be configured to check whether one or more validity criteria are satisfied. For example, the validity checker 2600 may be configured to perform an analysis pass over the generated structured data representation. In some implementations, the validity checker 2600 may be configured to perform the analysis pass over the generated structured data representation by using one or more libraries and one or more programming language interpreters (e.g., one or more Python interpreters). For example, the validity checker 2600 may be configured to determine whether certain features (parameters or values) in the structured data representation satisfy certain validity criteria.

In some implementations, validity criteria associated with a particular activity for a biometric activity plan may be defined by a service provider, manufacturer of a computing device, etc. In some implementations, validity criteria associated with a particular activity for a biometric activity plan may be defined by a user. In some implementations, validity criteria associated with a particular activity for a biometric activity plan may be defined by physical fitness professionals or experts, medical professionals or experts, etc.

In some implementations, validity criteria associated with a particular activity for a biometric activity plan may be retrieved by the computing system (e.g., from an external source or external computing device including external data 2200), in response to the one or more machine-learned models 2400 generating the biometric activity plan. For example, the validity criteria may be obtained according to the type of activities that are provided in the biometric activity plan. For example, predetermined validity criteria may be stored in an external computing database, external computing device, server computing system, or at the computing system. As an example, predetermined validity criteria for a running activity plan may include a setting corresponding to a maximum distance, a setting for a maximum duration of time for running, a maximum total distance to run over a predetermined duration of time (e.g., over seven days), a maximum total time to run over a predetermined duration of time (e.g., over seven days), a maximum change (e.g., increase) in total distance to run over a predetermined duration of time (e.g., over seven days), a maximum change (e.g., increase) in total time to run over a predetermined duration of time (e.g., over seven days), etc. As described herein, the values for the predetermined validity criteria can be defined and stored beforehand and may be associated with traits of users (e.g., associated with demographics of users). In some implementations, the predetermined validity criteria may be customized according to traits of the user associated with the computing system.

For example, the validity criteria may be set to values which can help prevent or reduce injuries which a user may experience by partaking in a particular activity (once or over multiple times during a predetermined duration of time), which can improve the safety of carrying out a particular activity (once or over multiple times during a predetermined duration of time), which can increase the likelihood that the user will complete the activity, which can increase the likelihood that the user will repeat the activity, etc. For example, the validity criteria may be set to values so that the biometric activity plan that is output to the user will likely be accepted and not rejected (e.g., as being unsafe, unreasonable, impractical, etc.). By utilizing the validity criteria to reject biometric activity plans initially generated via the one or more machine-learned models which the user would have likely rejected, computing resources can be conserved (e.g., bandwidth, network resources, processing power, etc.) because the computing system will not transmit a biometric activity plan that is not valid and because the user will not have to reject the biometric activity plan and request another biometric activity plan be generated.

FIG. 4B illustrates an example analysis pass, according to examples of the disclosure. The example analysis pass 4200 includes functions which evaluate whether an increase in a training load increases beyond a threshold value (e.g., more than 15%) within a predetermined duration of time (e.g., over consecutive 7 day periods).

For example, a first function determines total load based on a workout plan for a week. The first function iterates through each day's plan ("StructuredDailyPlan") in the weekly plan. For each activity in a daily plan, if the activity is an instance of "Exercise," the duration of the exercise is added to the total load. For each activity in the daily plan, if the activity is an instance of "CompoundExercise," the first function iterates through the exercises and adds the duration multiplied by the repetitions to the total load. Then an accumulated total load is returned.

For example, a second function iterates through each 7-day window in the workout plan ("workout_plan") using the range function. The second function extracts two consecutive weeks ("week1" and "week2") from the workout plan and calculates the total load for each week using the "calculate_total_load" function. The second function checks if the increase in load from week 1 to week 2 exceeds 15% of the load in week 1. If the constraint (validity criteria) is violated for any window, a "False" output may be returned while if the constraint is satisfied, a "True" output may be returned.

As described with respect to the example of FIG. 4B, when the analysis does not pass, the method 3000 may return via a feedback loop from operation 3400 to operation 3200 for an updated biometric activity plan to be generated. The updated biometric activity plan may be generated at operation 3200 using feedback information that is obtained based on the result of the analysis conducted at operation 3400. For example, the feedback information may include information regarding which validity criteria was not satisfied, regarding particular activities that did not satisfy certain validity criteria, etc.

As described with respect to the example of FIG. 4B, when the analysis does pass, the method 3000 may proceed to operation 3500 and the biometric activity plan may be output to the user, for example, via the output device 126. For example, the biometric activity plan may be presented via a graphical user interface. As another example, the biometric activity plan may be presented via a speaker. As described herein, example biometric activity plans may include one or more recommendations for performing one or more activities. The one or more activities may include exercise activities including walking, running, swimming, cycling, weightlifting, etc. The one or more activities may include a sleep schedule, a nap schedule, etc. The one or more activities may include dietary activities, including meal plans, recommended foods or beverages for consumption, eating schedules (e.g., recommended times to eat), etc.

Figure 5:
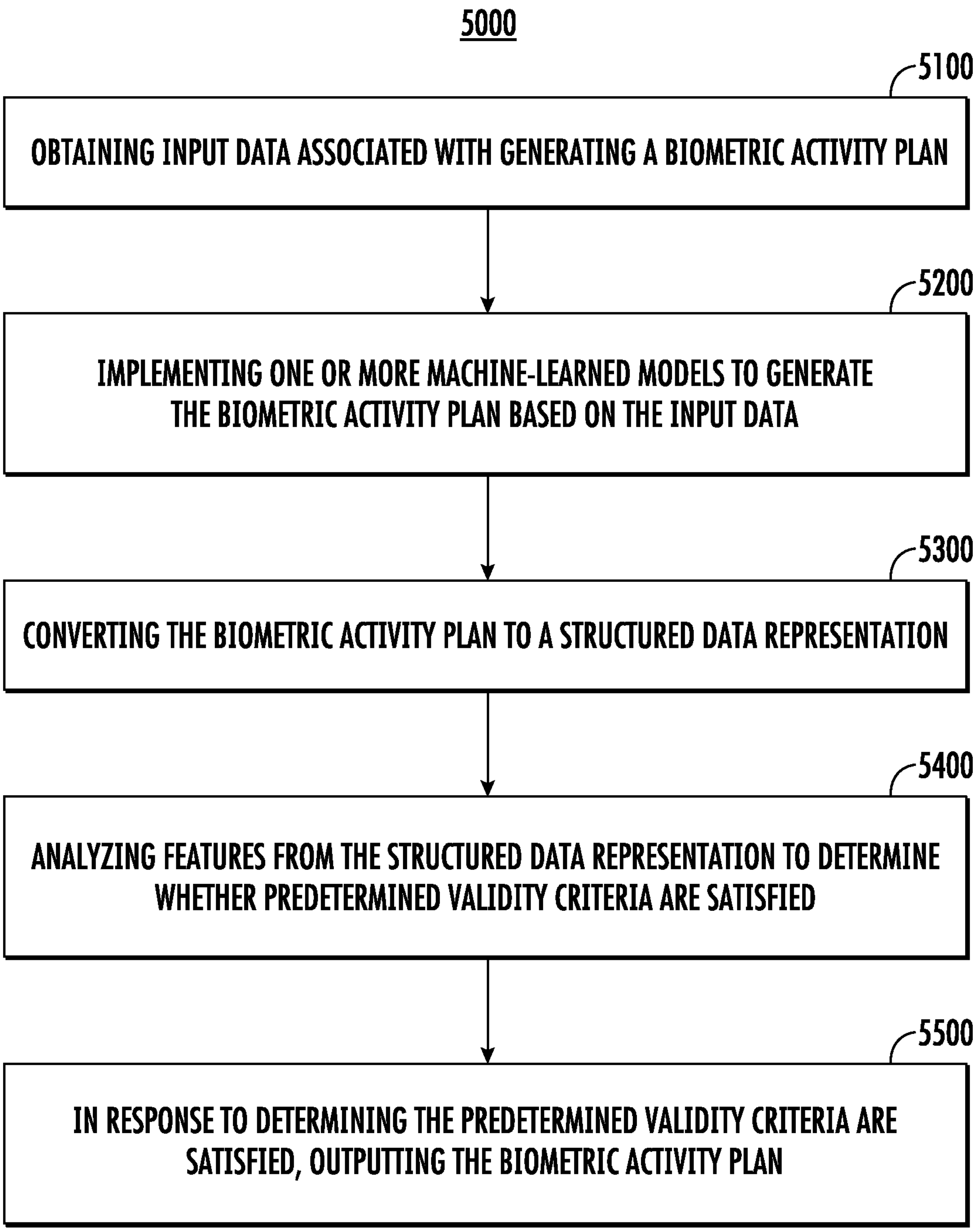
FIG. 5 is a flow diagram of an example, non-limiting computer-implemented method according to one or more examples of the disclosure.

FIG. 5 illustrates an example flow diagram of a non-limiting computer-implemented method for generating a biometric activity plan for a user, according to one or more examples of the disclosure.

The flow diagram of FIG. 5 illustrates a method 5000 for generating a biometric activity plan for a user. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At operation 5100 the method 5000 includes obtaining, by a computing system, input data associated with generating a biometric activity plan. For example, the computing system can include the user computing system 102 and/or the server computing system 130. For example, the input data can be provided to biometric activity application 124. The input data may include information from a query provided by a user, information from the user information data store 170, information associated with the sensor data 2100, and/or information associated with the external data 2200. For example, the user input component 122 may be configured to receive an input from a user requesting the biometric activity plan, and the input data may be obtained in response to receiving the input. In some implementations, obtaining the input data relating to the biometric activity plan is performed automatically in response to an occurrence of a predetermined event, or according to a predetermined time, as described herein.

At operation 5200 the method 5000 includes implementing, by the computing system, one or more machine-learned models to generate the biometric activity plan based on the input data. The one or more machine-learned models may include large language models, sequence processing models, generative machine-learned models, neural networks, etc.

For example, one or more sequence processing models may be configured to receive an input including text and tokenize the input by breaking down the sequence of text into small units (tokens) to provide a structured representation of the input sequence. The one or more sequence processing models may represent the tokens as vectors in a continuous vector space by mapping each token to a high-dimensional vector, where the relationships between tokens (words) are reflected in the geometric relationships between their corresponding vector. As an example, the one or more sequence processing models may receive an input including the text "I want a weightlifting plan to gain muscle mass" and tokenize the input by breaking down the sequence of text into small units (tokens) (e.g., "weightlifting," "plan," "gain," "muscle," and "mass"), thereby providing a structured representation of the input sequence. In a word embedding, semantically similar words are closer together in the vector space. For example, the vectors for "gain" and "increase" might be close to each other because of their semantic relationship, while the vectors for "gain" and "decrease" may be far apart compared to the vectors for "gain" and "increase."

For example, the query may include a request to generate a biometric activity plan and the one or more sequence processing models may be configured to tokenize and embed the query and infer a value for the query, based on semantic relationships with other vectors in the vector space, and based on other data that is represented as vectors in the vector space (e.g., input sequence data which may include raw data relating to what may generally be considered as a gaining muscle mass) to infer that increasing muscle mass may include losing a certain percentage of body fat.

The one or more machine-learned models may be configured to generate conditioning parameters based on the query, wherein the conditioning parameters provide values for one or more conditions associated with a biometric activity plan (or for one or more activities in the biometric activity plan) to be rendered. To generate the conditioning parameters, values for the one or more conditions may be determined based on inferred values for the one or more conditions, based on predicted values for the one or more conditions, based on current values for the one or more conditions, and/or based on historical values for the one or more conditions. The query may include information indicative of the user's intent or requirements.

In some implementations, the computing system may be configured to implement one or more large language models to determine a plurality of variables based on the query. For example, the one or more large language models may include a Bidirectional Encoder Representations from Transformers (BERT) large language model. The one or more large language models may be trained to understand and process natural language for example. The one or more large language models may be configured to extract information from the query to identify keywords, intents, and context within the query to determine a plurality of variables for generating the biometric activity plan. The variables may include latent variables that represent an underlying structure of the language.

For example, the biometric activity application 124 may be configured to utilize one or more forecasting methods (e.g., linear regression, autoregressive-integrated moving average models, exponential smoothing state space models) and/or neural networks (long short-term memory networks, gated recurrent unit networks, feedforward neural networks, etc.) for determining values for the one or more conditions based on current values and/or historical values for the one or more conditions.

For example, to generate a biometric activity plan satisfying various conditions (e.g., losing five pounds in one month) according to one or more values, the one or more generative machine-learned models may be configured to generate a biometric activity plan that is predicted to satisfy the query based on values for one or more conditions (e.g., values for distances to run each week over the course of the month, values for a number of calories to consume, etc.).

The one or more generative machine-learned models may include a deep neural network or a generative adversarial network (GAN) to generate the biometric activity plans with values for conditions associated with activities included in the biometric activity plans. For example, the computer system may include a database which is configured to store a plurality of generative machine-learned models respectively associated with a plurality of different biometric activity plans. The computing system may be configured to retrieve, from among the one or more generative machine-learned models, a generative machine-learned model associated with a particular activity relating to the query.

In some implementations, the one or more generative machine-learned models may be trained on a large dataset of biometric activity plans with corresponding information about the conditions associated with one or more activities. These conditions could include variables like time of day, exercise goals, a number of repetitions to perform, an amount of time to spend on the activity, a number of sets to perform, a distance to travel, etc. During training, the one or more generative machine-learned models may be configured to learn relationships between the biometric activity plans and conditions that influence them. This may involve the computer system adjusting each generative machine-learned model's internal parameters to generate realistic biometric activity plans based on the training data. The one or more generative machine-learned models may be trained on one or more training datasets including a plurality of reference biometric activity plans. The one or more training datasets may include values for one or more conditions for at least some of the plurality of reference biometric activity plans. The reference biometric activity plans may be associated with a particular activity (e.g., sleeping, running, swimming, cycling, weightlifting, etc.), for example. The reference biometric activity plans may be associated with a particular goal (e.g., to lose a certain amount of weight, to increase muscle mass, to improve performance with respect to an activity a certain amount), for example.

At operation 5300 the method 5000 includes converting the biometric activity plan to a structure data representation. For example, as described herein the structured data representation generator 2500 may be configured to convert text output by the one or more machine-learned models 2400 by parsing the text using string manipulation or regular expressions to extract relevant information from the text. For example, certain information may be extracted and mapped to a particular dictionary to hold the extracted information.

As an example, if a biometric activity plan output in text form by the one or more machine-learned models 2400 includes performing an exercise for two minutes, the dictionary used to generate the structured data representation may have an object that corresponds to a "duration" with a property that has a value of "two minutes". In some implementations, the structured data representation may be in a JSON (JavaScript Object Notation) structured data format. For example, the biometric activity plan generated by the one or more machine-learned models may be in a text format, and converting the biometric activity plan to the structured data representation may include the biometric activity application 124 parsing the biometric activity plan to determine features included in the structured data representation.

At operation 5400 the method 5000 includes analyzing features from the structured data representation to determine whether predetermined validity criteria are satisfied. For example, as described herein the validity checker 2600 may be configured to check whether one or more validity criteria are satisfied. For example, the validity checker 2600 may be configured to perform an analysis pass over the generated structured data representation. In some implementations, the validity checker 2600 may be configured to perform the analysis pass over the generated structured data representation by using one or more libraries and one or more programming language interpreters (e.g., one or more Python interpreters). For example, the validity checker 2600 may be configured to determine whether certain features (parameters or values) in the structured data representation satisfy certain validity criteria. In some implementations, the biometric activity application 124 may be configured to retrieve the predetermined validity criteria (e.g., from an external computing device) in response to the biometric activity plan being generated.

For example, the biometric activity plan may include one or more activities, and the predetermined validity criteria may include a respective threshold level of activity for each activity in the biometric activity plan. The biometric activity application 124 may be configured to determine whether the predetermined validity criteria are satisfied by determining, for each activity in the biometric activity plan, whether a level for the activity exceeds the respective threshold level of activity. For example, the biometric activity plan may include one or more activities, and the predetermined validity criteria may include a respective threshold increase in a level of activity for each activity in the biometric activity plan over a predetermined duration of time. The biometric activity application 124 may be configured to determine whether the predetermined validity criteria are satisfied by determining, for each activity in the biometric activity plan, whether an increase in a level for the activity over the predetermined duration of time exceeds the respective threshold increase in the level of activity.

At operation 5500 the method 5000 includes in response to determining the predetermined validity criteria are satisfied, outputting the biometric activity plan. For example, when the analysis does pass (e.g., the predetermined validity criteria are satisfied), the biometric activity plan may be output to the user, for example, via output device 126. For example, the biometric activity plan may be presented via a graphical user interface. As another example, the biometric activity plan may be presented via a speaker. When the analysis does not pass (e.g., the predetermined validity criteria are not satisfied), the one or more machine-learned models 2400 may be implemented to generate an updated biometric activity plan based on the input data and based on the features from the structured data representation which do not satisfy the predetermined validity criteria. For example, the updated biometric activity plan may be generated using feedback information that is obtained based on the result of the analysis. For example, the feedback information may include information regarding which validity criteria was not satisfied, regarding particular activities that did not satisfy certain validity criteria, etc.

As mentioned above, aspects of the disclosure have been described in view of the biometric activity application 124 provided in the user computing system 102. However, some or all of those aspects can also be applied to the biometric activity application 142 provided in the server computing system 130, and thus some or all of the functions and operations of the biometric activity application 124 may also be applied and carried out by the biometric activity application 142 in a similar fashion but will not be described again for the sake of brevity.

Aspects of the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks, Blue-Ray disks, and DVDs; magneto-optical media such as optical discs; and other hardware devices that are specially configured to store and perform program instructions, such as semiconductor memory, read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the non-transitory computer-readable storage media may also be embodied in at least one application specific integrated circuit (ASIC) or Field Programmable Gate Array (FPGA).

Each block of the flowchart illustrations may represent a unit, module, segment, or portion of code, which comprises one or more executable instructions for implementing the specified logical function(s). It should also be noted that in some alternative implementations, the functions noted in the blocks may occur out of order. For example, two blocks shown in succession may in fact be executed substantially concurrently (simultaneously) or the blocks may sometimes be executed in the reverse order, depending upon the functionality involved.

While the disclosure has been described with respect to various example embodiments, each example is provided by way of explanation, not limitation of the disclosure. Those skilled in the art, upon attaining an understanding of the foregoing, can readily produce alterations to, variations of, and equivalents to such embodiments. Accordingly, the disclosure does not preclude inclusion of such modifications, variations and/or additions to the disclosed subject matter as would be readily apparent to one of ordinary skill in the art. For example, features illustrated or described as part of one embodiment can be used with another embodiment to yield a still further embodiment. Thus, it is intended that the disclosure covers such alterations, variations, and equivalents.

What is claimed is:

1. A computing system, comprising:

one or more memories configured to store one or more instructions; and one or more processors configured to execute the one or more instructions stored in the one or more memories to perform operations, the operations comprising:

obtaining input data associated with generating a biometric activity plan, implementing one or more machine-learned models to generate the biometric activity plan based on the input data, converting the biometric activity plan to a structured data representation by parsing text comprising the biometric activity plan to obtain one or more data classes with one or more associated attributes representing features of the biometric activity plan, comparing, by a validity checker of the computing system, features from the structured data representation with predetermined validity criteria associated with one or more activities included in the biometric activity plan to determine whether the predetermined validity criteria are satisfied, based on determining the predetermined validity criteria are satisfied, outputting the biometric activity plan for presentation to a user via a user interface, and based on determining the predetermined validity criteria are not satisfied and prior to the biometric activity plan being output for presentation to the user via the user interface, processing, by the one or more machine-learned models, the input data and feedback information including the features from the structured data representation which do not satisfy the predetermined validity criteria, to generate an updated biometric activity plan for presentation to the user via the user interface.

2. The computing system of claim 1, wherein the operations further include:

based on the biometric activity plan being generated, retrieving the predetermined validity criteria from one or more databases according to the one or more activities included in the biometric activity plan, and wherein the predetermined validity criteria comprises a threshold level of activity for a first activity among the one or more activities, and the validity checker is configured to compare a planned level of activity for the first activity among the one or more activities included in the biometric activity plan with the threshold level of activity for the first activity to determine whether the predetermined validity criteria are satisfied.

3. The computing system of claim 1, further comprising:

a user input component configured to receive an input from the user requesting the biometric activity plan, wherein the input data is obtained in response to receiving the input.

4. The computing system of claim 1, wherein obtaining the input data relating to the biometric activity plan is performed automatically in response to an occurrence of a predetermined event.

5. The computing system of claim 4, wherein the predetermined event includes a determination by the computing system that the user has experienced a biological change in state.

6. The computing system of claim 1, wherein the predetermined validity criteria includes a respective threshold level of activity for each activity among the one or more activities included in the biometric activity plan, and determining, by the validity checker, whether the predetermined validity criteria are satisfied includes determining, for each activity among the one or more activities included in the biometric activity plan, whether a level for the activity exceeds the respective threshold level of activity.

7. The computing system of claim 1, wherein the biometric activity plan includes one or more activities, the predetermined validity criteria includes a respective threshold increase in a level of activity for each activity among the one or more activities included in the biometric activity plan over a predetermined duration of time, and determining, by the validity checker, whether the predetermined validity criteria are satisfied includes determining, for each activity among the one or more activities included in the biometric activity plan, whether an increase in a level for the activity over the predetermined duration of time exceeds the respective threshold increase in the level of activity.

8. The computing system of claim 1, wherein the structured data representation is in a JavaScript Object Notation form.

9. The computing system of claim 1, wherein an output corresponding to the biometric activity plan generated by the one or more machine-learned models prior to converting the biometric activity plan to the structured data representation is decoupled from the biometric activity plan which is output for presentation to the user based on determining the predetermined validity criteria are satisfied.

10. The computing system of claim 1, wherein the operations include, based on the biometric activity plan being generated, retrieving the predetermined validity criteria from an external computing device.

11. A computer-implemented method, comprising:

obtaining, by a computing system, input data associated with generating a biometric activity plan, implementing, by the computing system, one or more machine-learned models to generate the biometric activity plan based on the input data, converting, by the computing system, the biometric activity plan to a structured data representation by parsing text comprising the biometric activity plan to obtain one or more data classes with one or more associated attributes representing features of the biometric activity plan, comparing, by a validity checker of the computing system, features from the structured data representation with predetermined validity criteria associated with one or more activities included in the biometric activity plan to determine whether the predetermined validity criteria are satisfied, based on determining the predetermined validity criteria are satisfied, outputting, by the computing system, the biometric activity plan for presentation to a user via a user interface, and based on determining the predetermined validity criteria are not satisfied and prior to the biometric activity plan being output for presentation to the user via the user interface, processing, by the one or more machine-learned models, the input data and feedback information including the features from the structured data representation which do not satisfy the predetermined validity criteria, to generate an updated biometric activity plan for presentation to the user via the user interface.

12. The computer-implemented method of claim 11, further comprising:

based on the biometric activity plan being generated, retrieving the predetermined validity criteria from one or more databases according to the one or more activities included in the biometric activity plan, and wherein the predetermined validity criteria comprises a threshold level of activity for a first activity among the one or more activities, and the computer-implemented method further comprises comparing, by the validity checker, a planned level of activity for the first activity among the one or more activities included in the biometric activity plan with the threshold level of activity for the first activity to determine whether the predetermined validity criteria are satisfied.

13. The computer-implemented method of claim 11, further comprising:

receiving, via a user input component of the computing system, an input from the user requesting the biometric activity plan, wherein the input data is obtained in response to receiving the input.

14. The computer-implemented method of claim 11, wherein obtaining the input data relating to the biometric activity plan is performed automatically in response to an occurrence of a predetermined event, and the predetermined event includes a determination by the computing system that the user has experienced a biological change in state.

15. The computer-implemented method of claim 11, wherein the predetermined validity criteria includes a respective threshold level of activity for each activity among the one or more activities included in the biometric activity plan, and determining, by the validity checker, whether the predetermined validity criteria are satisfied includes determining, for each activity among the one or more activities included in the biometric activity plan, whether a level for the activity exceeds the respective threshold level of activity.

16. The computer-implemented method of claim 11, wherein the predetermined validity criteria comprises a respective threshold increase in a level of activity for each activity among the one or more activities included in the biometric activity plan over a predetermined duration of time, and determining, by the validity checker, whether the predetermined validity criteria are satisfied further comprises determining, for each activity among the one or more activities included in the biometric activity plan, whether an increase in a level for the activity over the predetermined duration of time exceeds the respective threshold increase in the level of activity.

17. The computer-implemented method of claim 11, wherein an output corresponding to the biometric activity plan generated by the one or more machine-learned models prior to converting the biometric activity plan to the structured data representation is decoupled from the biometric activity plan which is output for presentation to the user based on determining the predetermined validity criteria are satisfied.

18. The computer-implemented method of claim 12, further comprising:

based on the biometric activity plan being generated, retrieving the predetermined validity criteria from an external computing device.

19. A non-transitory computer-readable medium which stores instructions that are executable by one or more processors of a computing system, the instructions comprising instructions to cause the one or more processors to perform operations, the operations comprising:

obtaining input data associated with generating a biometric activity plan, implementing one or more machine-learned models to generate the biometric activity plan based on the input data, converting the biometric activity plan to a structured data representation by parsing text comprising the biometric activity plan to obtain one or more data classes with one or more associated attributes representing features of the biometric activity plan, comparing, by a validity checker of the computing system, features from the structured data representation with predetermined validity criteria associated with one or more activities included in the biometric activity plan to determine whether the predetermined validity criteria are satisfied, based on determining the predetermined validity criteria are satisfied, outputting the biometric activity plan for presentation to a user via a user interface, and based on determining the predetermined validity criteria are not satisfied and prior to the biometric activity plan being output for presentation to the user via the user interface, processing, by the one or more machine-learned models, the input data and feedback information including the features from the structured data representation which do not satisfy the predetermined validity criteria, to generate an updated biometric activity plan for presentation to the user via the user interface.

* * * * *